United States Patent [19]

Garris

[11] Patent Number: 4,932,396
[45] Date of Patent: Jun. 12, 1990

[54] ELLIPTICAL RING SPLINT WITH SPACER

[76] Inventor: Cynthia G. Garris, 211 Robertson Ave., Charlottesville, Va. 22903

[21] Appl. No.: 182,296

[22] Filed: Apr. 15, 1988

Related U.S. Application Data

[63] Continuation-in-part of Ser. No. 927,444, Jun. 6, 1987, Pat. No. 4,770,166.

[51] Int. Cl.$^5$ .............................................. A61F 5/10
[52] U.S. Cl. ................................. 128/77; 128/87 A; 128/89 R
[58] Field of Search ................ 128/87 A, 77, 89 R

[56] References Cited

U.S. PATENT DOCUMENTS

| | | | |
|---|---|---|---|
| 3,170,460 | 2/1965 | Stilson | 128/77 |
| 4,220,334 | 9/1980 | Kanamoto et al. | 128/77 X |
| 4,243,026 | 1/1981 | Barber | 128/87 A X |
| 4,270,528 | 6/1981 | Hanson | 128/87 A |
| 4,297,992 | 11/1981 | LaRue et al. | 128/87 A X |
| 4,441,489 | 4/1984 | Evans et al. | 128/87 A X |
| 4,770,166 | 9/1988 | Garris | 128/87 A X |

FOREIGN PATENT DOCUMENTS

| | | | |
|---|---|---|---|
| 1529910 | 6/1968 | France | 128/77 |
| 1195998 | 12/1985 | U.S.S.R. | 128/77 |

Primary Examiner—Robert A. Hafer
Assistant Examiner—Kevin G. Rooney
Attorney, Agent, or Firm—John J. Byrne; Bradford E. Kile; Ruffin B. Cordell

[57] ABSTRACT

An adjustable splint made of silver or gold alloys for stabilizing in extension or realigning the interphalangeal joints of the fingers and thumb consisting of two elliptical rings joined by an elliptical spacer. The individually sized proximal and distal elliptical rings are worn about the fingers on either side of the joint being splinted and disposed at an angle with respect to the axis of the finger. The rings are joined by an elliptical spacer which is placed over the dorsal surface of the joint and sized to distribute and spread the pressure uniformly and comfortably over the surface of the joint. The spacer acts in conjunction with the proximal and distal rings to hold the finger in varying degrees of extension, depending on the adjustment of the splint. The splint may be rotated 90°, placing the spacer on the lateral border of a joint to realign an angularly deviated joint.

7 Claims, 2 Drawing Sheets

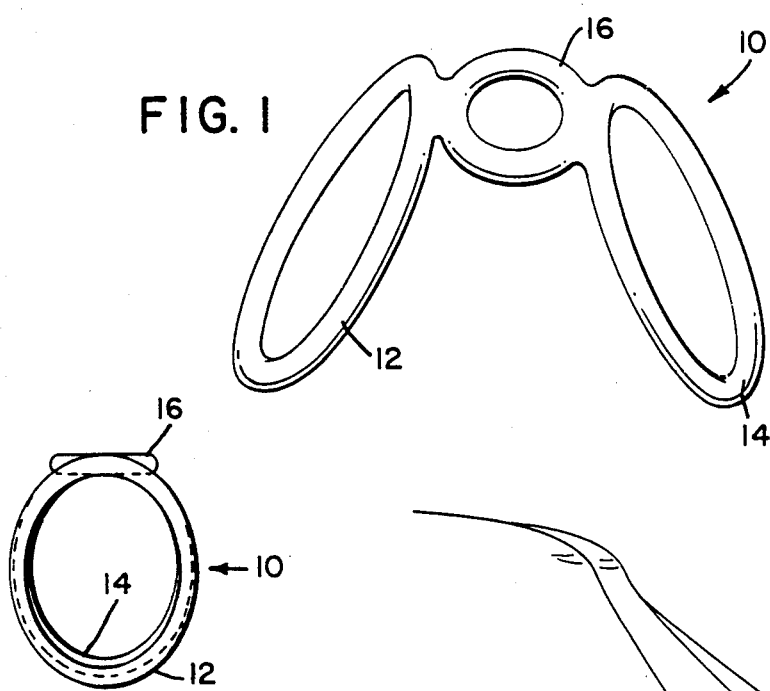
FIG. 1
FIG. 1a
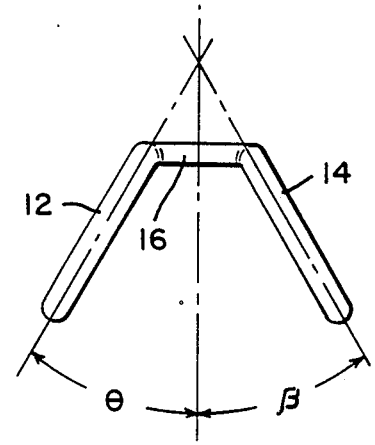
FIG. 2
FIG. 3
FIG. 4
FIG. 5

ELLIPTICAL RING SPLINT WITH SPACER

BACKGROUND AND FIELD OF THE INVENTION

1. Field of Invention

This application is a continuation-in-part of my co-pending application, Ser. No. 927,444, filed June 6, 1987, now U.S. Pat. No. 4,770,166 entitled ELLIPTICAL FINGER RING SPLINT. The present invention relates to the field of orthotics, and particularly to splint devices wherein individual elliptical rings are joined by an elliptical spacer to make a ring type splint used for straightening, holding in extension, or realigning one or more of the joints of the fingers or thumb.

2. Description of the Prior Art

In normal hand use, various static and dynamic forces are exerted on the finger joints. Deformity or instability of joints due to injuries or disease results in fuctional losses in the hand. Among the finger deformities caused by diseased processes are flexion contracture deformities. These are known as boutonniere or mallet finger deformities. Another type are angulation deformities, known as lateral deviation deformities. These deformities all cause pain and instability in all fingers. In the thumb, there is a resultant loss of pinch strength. This is particularly troublesome since the thumb accounts for more than 50% of the function of the hand.

In juvenile rheumatoid arthritis (JRA), the boutonniere deformity results from inflammation at the proximal interphalangeal (PIP) joint. This inflammation damages and weakens the tendons and ligaments causing them to slip out of their normal line of pull.

In advanced stages of rheumatoid arthritis, the interphalangeal (IP) joints have boney errosions and ligamentous laxity. Angulation deformities and severe losses of strength and dexterity results when external lateral forces are placed on these joints.

Individuals with cerebral palsy often have spasticity in their hands which causes their interphalangeal (IP) joints to remain in flexion. This severely limits purposeful use of the hand for even the simplest task, such as pressing computer keys.

In all of the above conditions and in similar conditions, a splint type device to hold the finger in extension or realign an angularly deviated finger is desirable for improved hand function. A principal objective of this invention is to satisfy that need.

Many types of splints have been designed and marketed over the years. These prior art splints share one or more undesirable attributes. Typically, such splints are manufactured from bulky splinting materials that include various cumbersome strapping devices and oftentimes use wire outriggers. In addition, the prior art splints pose a variety of functional difficulties. They are generally difficult to get on and off because of their bulkiness. Also, they cause the fingers to abduct (spread out) when wearing them. Many also limit or prevent basic daily activities such as having one's hands in water, wearing gloves, or placing one's hands in a clothing pocket.

DESCRIPTION OF RELATED ART

Although prior art splints have acceptance in some settings such as a hand rehabilitation program where therapeutic goals are short-term, they are unacceptable when long-term splinting is desirable or required.

A primary objective of this invention is to provide a lightweight, non-bulky splint that will not cause abduction (the spreading out) of the fingers when all fingers are splinted at the same time. Splint are oftentimes used on a multi-finger arrangement wherein the invention described herein produces less interference with the movement of other joints on the same or adjacent fingers.

Another primary objective of this invention is to provide a splint wherein an elliptical spacer is placed over the dorsal surface of a joint. The spacer, in cooperation with two elliptical rings about the finger, provides a straightening force to the finger.

Another important objective of this invention is to provide a splint of the type described which can be applied to fingers having a lateral misalignment by placing the elliptical spacer against the protruding joint. This, in cooperation with the elliptical rings about the fingers, will align the finger and the spacer will diffuse the aligning pressure.

A further objective of this invention is to provide an orthotic device which is attractive in appearance and does not appear as an orthotic appliance. In many instances, patients are likely to wear attractive appliances for a longer period of time than appliances that draw attention to their deformities.

A still further objective of this invention is to provide a splint that can be manufactured from durable, nonallergenic, easily-cleaned materials that are impervious to the effects of water.

Another objective of the invention is to provide easy adjustability for minor changes in finger size that may result from swelling.

A still further objective of the invention is to provide stability of the finger joints in a functional alignment by providing an elliptical connector between elliptical finger rings.

Another objective of the invention is to provide a splint that will not require removal to perform daily activities such as bathing or wearing gloves. It will be seen that a new splint is described herein to replace the prior art splints that have not provided a fully-acceptable solution for long-term splinting needs for individuals that have boutonniere, mallet finger and angular deviation deformities.

These and other objectives and advantages of the invention will be evident from the following description when read in light of the drawings.

BRIEF DESCRIPTION OF THE DRAWINGS

FIG. 1 is a perspective view of a finger splint in accordance with this invention;

FIG. 1a is an end view showing angles;

FIG. 2 is a side view of FIG. 1;

FIG. 3 is a view in which a splint is carried on each of adjacent fingers;

FIG. 4 is a side view of a deformed finger;

FIG. 5 is a perspective view showing the splint on a distal interphalangeal joint of the finger shown in FIG. 4;

DESCRIPTION OF THE PREFERRED EMBODIMENT

Figure 6:
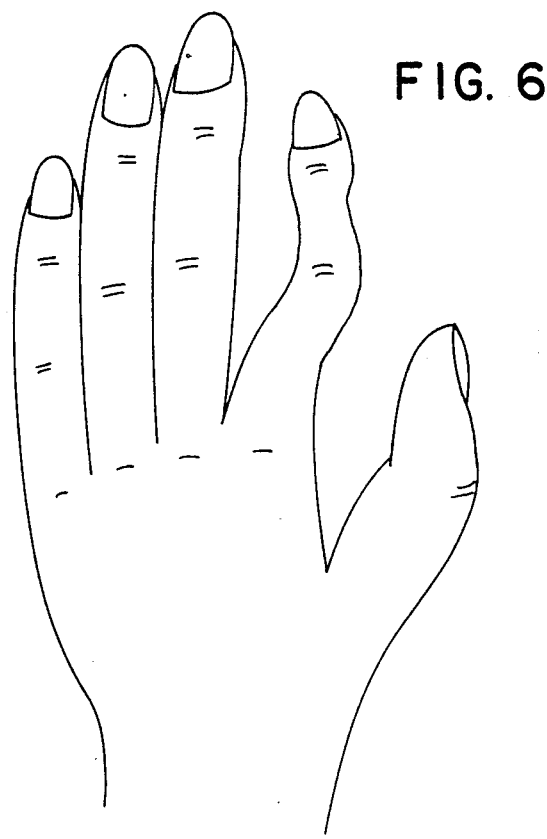
FIG. 6 is a plan view of a finger having a lateral deformation.

Referring now to the drawings wherein like numerals refer to like elements, the adjustable finger splint of the present invention is indicated by the numeral 10. The splint is a three ring type consisting of an elliptical proximal ring 12 and an elliptical distal ring 14 joined by an elliptical spacer 16. This splint is designed to straighten and/or realign a finger joint that has been adversely affected by injury or disease.

The splint is appropriate for various joints of the fingers and thumb. As used herein and in the appended claims, the term "joint(s)" refers to the joint(s) being splinted and not to the other, unaffected joint(s) of the fingers and/or thumb unless specifically stated. Furthermore, the word "joint(s)" encompasses the thumb interphalangeal (IP) joint, and the proximal interphalangeal (PIP) and distal interphalangeal (DIP) joints of the finger(s). Additionally, the term "finger" is meant to include all digits of the hand, including the thumb unless separately identified.

The rings 12 and 14 and the spacer 16 are formed from malleable, generally precious, metals such as silver and gold. Such metals, and alloys thereof, are firm but deformable. From these metals, the elliptical rings 12 and 14 are formed, each being sized individually to provide a custom fit to the finger joint being splinted. The proximal ring 12 and distal ring 14 are sized to fit comfortably and firmly, and are not sized to tightly encircle the finger on either side of the joint to be spanned. The rings are worn at an angle of between 15°–45° with respect to a vertical axis 18 through the joint. The rings 12 and 14 are joined by an elliptical spacer 16 which impinges on either the dorsal or lateral surface of the joint, depending on the deformity splinted.

When the splint is worn with the spacer over the dorsal (upper) surface of the joint as seen in FIGS. 3 and 5, reducible (flexible) flexion deformities (boutonniere and mallet finger deformities) are blocked and the finger is held in extension. When the splint is worn with the spacer on a lateral side of the joint as seen in FIG. 5, reducible misalignments in the lateral plane (angulation or lateral deviation deformities) are straightened by providing support and applying pressure on the side of the joint opposite the direction of angulation.

The splint 10 is used to extend or realign (straighten) a joint as seen in FIG. 5. Here, the spacer 16 distributes and diffuses the pressures over the splinted joint as it acts in conjunction with the other rings to provide corrective action.

For the corrective force to be applied comfortably, it is important that the area of contact with the joint be spread or diffused to reduce pressure at any particular point and yet remain attractive and jewelry-like. An important aspect of the elliptical spacer of the present invention is that it is individually sized to distribute the pressure uniformly and comfortably over the joint being splinted. The pressure distribution of the present device is accomplished through the shape and size of the custom spacer. Custom sizing is particularly important for realignment of advanced stage deformities that rarely fit into normal ranges.

The proximal ring 12 and the distal ring 14 have elliptical shapes and are worn at an angle with respect to the axis of the finger. The proximal elliptical ring is custom-fitted to the proximal side of the joint being splinted, and the distal elliptical ring is custom-fitted to the distal side of the joint being splinted. The elliptical shape and custom sizing of these rings provide a conforming shape which firmly, but comfortably, surrounds the finger and stabilizes the joint in both the flexion-extension plane and the lateral plane.

The deformable nature of the materials from which this splint is fabricated allows for continuously variable adjustments by the wearer depending on the amount of corrective force desired. When the angle between the planes of the elliptical rings 12 and 14 and that of spacer 16 is decreased, the corrective force is decreased. Conversely, when the angle is increased the corrective force is increased.

When worn in the extension configuration, the splint is placed on the finger by inserting the finger through the openings of the two elliptical rings. The splint is moved until the elliptical spacer 16 is over the dorsal surface of the joint being splinted. The ends of the major axes of the proximal and distal elliptical rings are attached to the elliptical spacer. The rings extend, in their respective directions, away from the spacer and at an angle with respect to the axis of the finger. The other end of the major axis of these rings impinges on the palmer surface 20 of the finger.

When the elliptical spacer is over the dorsal surface of the joint, it applies a force against the joint toward the palmer surface of the hand. The proximal and distal elliptical rings impinging on the palmer surface apply a force on the finger on either side of the joint toward the dorsal surface of the hand. Together, these forces extend and straighten the splinted joint. The degree of extension is obtained by adjusting the angle between the planes of the elliptical rings.

Figure 7:
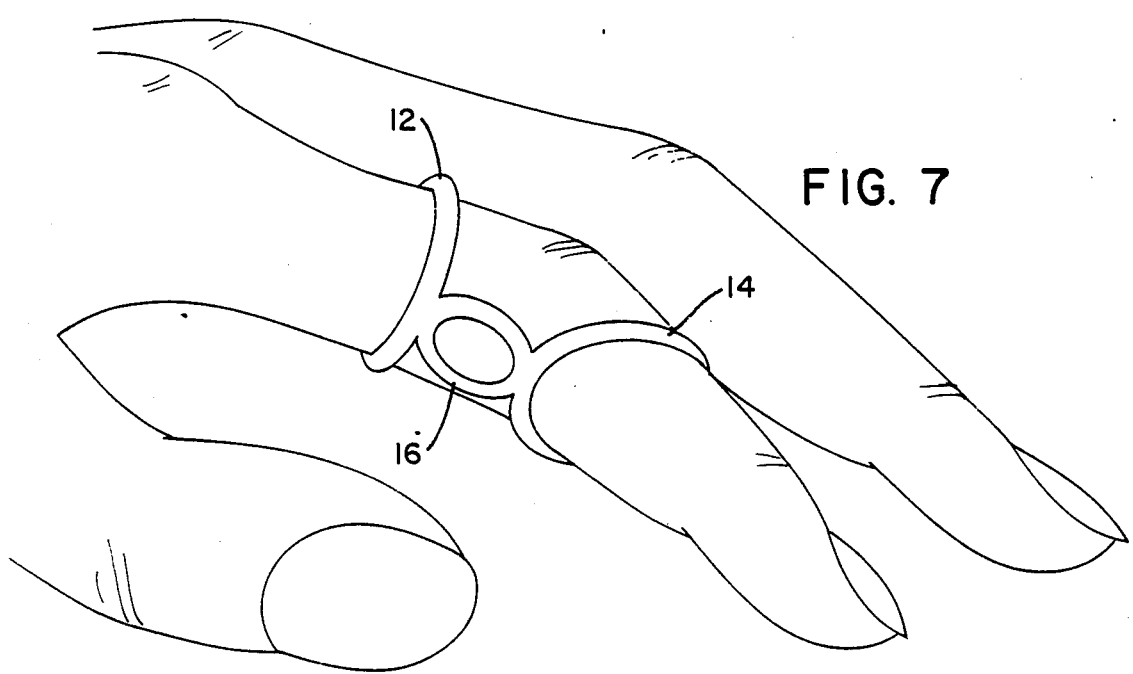
FIG. 7 is a view showing the splint with its spacer along the side of its finger.

When the splint is worn in the realignment configuration of FIG. 7 with the spacer on the lateral border of the joint to correct lateral deformation, a similar analysis of force components applies.

FIG. 4 is a side view of a finger deformed by an arthritic condition in the dorsal joint. In FIG. 5, the finger is shown with the splint applied. Note by way of the arrows 21 that pressure is spread and diffused over the entire sensitive joint by way of the spacer 16. Counter-pressures are taken up by the lower ends of the rings 12 and 14 on the less sensitive palm surface of the hand as denoted by the arrows 22 and 24.

Figure 6A:
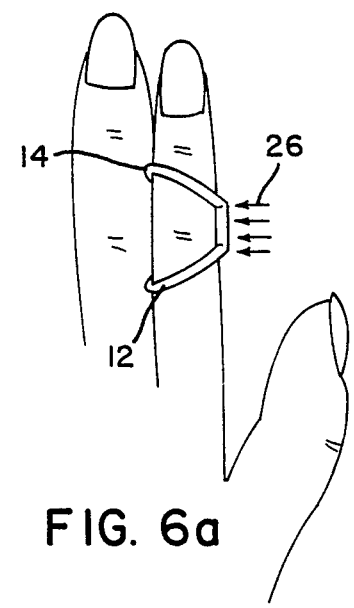
FIG. 6a is a view of the finger shown in FIG. 6 with a splint applied.

FIG. 6 shows a finger with a lateral deformation caused by arthritis or other disease. The splint of this invention can be used to correct this deformity as shown in FIG. 7. As seen by the plurality of arrows 26, in FIG. 6a, the finger can be held in a generally straight position and the pressure distributed by spacer 16.

In a general manner, while there has been disclosed an effective and efficient embodiment of the invention, it should be understood that the invention is not limited to such an embodiment as there might be changes made in the arrangement, disposition and form of the parts without departing from the principle of the present invention as comprehended within the scope of the accompanying claims.

I claim:

1. 1. A splint for straightening a finger having an angular deformation that divides the finger into a distal portion and a proximal portion which are angularly disposed with one another and from the finger's normal longitudinal axis, and said finger having a joint area formed where said portions join, the combination comprising:

a spacer ring adapted to be placed in contact with said joint area on the side opposite the direction of said angular deformation for distribution of contact force about said joint area;

a first elliptical ring disposed in a single plane and having a first edge attached to a first side of said spacer ring and being angularly disposed with respect to said spacer ring and sized to circumscribe said proximal portion of said finger;

a second elliptical ring disposed in a single plane and having a first edge attached to a side of said spacer ring opposite of said first side and being angularly disposed with respect to said spacer ring and sized to circumscribe said distal portion of said finger;

said spacer ring and said first and second elliptical rings being made of a malleable precious metal alloy of sufficient rigidity to bring said distal and proximal portions into alignment with said longitudinal axis when said spacer ring is in contact with said joint area.

2. The splint of claim 1 wherein said spacer and rings have a thickness permitting a lessening of interference between adjacent fingers during movement when each carries a splint.

3. The splint of claim 1 wherein said spacer is adapted to be located over the dorsal surface of a joint.

4. The splint of claim 1 wherein said spacer is adapted to be located on the lateral side of said finger.

5. The invention of claim 1 wherein the spacer ring is an ellipse having a major axis and a minor axis and the major axis of said spacer is perpendicular to said longitudinal axis.

6. The invention of claim 1 wherein the spacer ring is an ellipse having a major axis and a minor axis and the major axis of said spacer is parallel to said longitudinal axis.

7. A splint for straightening a finger that has an angular deformation that divides the finger into a distal portion and a proximal portion which are angularly disposed with one another and from the finger's normal longitudinal axis, and said finger having a joint area formed where said portions join, the combination comprising:

an elliptical joint contact ring having a plane generally parallel to said longitudinal axis;

a proximal elliptical ring having a major axis in the plane of said proximal elliptical ring and along its greatest length that intersects a first portion of said joint contact ring;

a distal elliptical ring having a major axis in the plane of said distal ring and along its greatest length that intersects a second portion of said joint contact ring;

said joint contact ring having an outer surface and an inner surface and having an axis through its geometric center perpendicular to the plane thereof and disposed for engagement with said joint area;

said joint contact ring adapted to be placed in contact with said joint area on the side opposite the direction of said angular deformation for distribution of contact force about said joint area;

means securing said first portion of said proximal ring to said joint contact ring in a manner so that the plane of said proximal ring is angularly disposed to the plane of said joint contact ring means securing said portion of said distal ring to said joint contact ring in a manner so that the plane of said distal ring is angularly disposed to the plane of said joint contact ring and said first and second planes intersect above said outer surface;

said distal and proximal rings approximate the dimensions of the finger to be corrected;

said spacer and said proximal and distal elliptical rings being made of a deformable metal alloy attractive in appearance and of sufficient rigidity to hold said distal and proximal portions of said finger in close alignment with said longitudinal axis when said spacer is in contact with said enlarged area.

* * * * *